United States Patent
Pflaum et al.

(12) 
(10) Patent No.: US 6,696,086 B1
(45) Date of Patent: Feb. 24, 2004

(54) SOLID PHARMACEUTICAL FORMULATION CONTAINING LOVASTATIN AND SIMVASTATIN, RESPECTIVELY, AND ITS PREPARATION

(75) Inventors: Zlatko Pflaum, Domzale (SI); Mateja Salobir, Ljubljana (SI); Zdenka Jerala, Mavcice (SI); Aleksander Resman, Kogojeva (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 09/657,853

(22) Filed: Sep. 8, 2000

(30) Foreign Application Priority Data

Sep. 10, 1999 (SI) .................................. 9900211

(51) Int. Cl.$^7$ ................................ A61K 9/20
(52) U.S. Cl. ........................ 424/464; 424/460; 424/474; 424/489; 424/451
(58) Field of Search .......................... 514/460; 424/489, 424/472, 464, 451, 400, 474

(56) References Cited

U.S. PATENT DOCUMENTS 6,235,311 B1 * 5/2001 Ullah et al. ................. 424/472

OTHER PUBLICATIONS

Pavia, Donald L., Lampman, Gary M, Kriz, Jr., George S., Introduction to Organic Laboratory Techniques, A Contemporary Approach, 1982, Second Edition, pp. 489–490.*

Zubrick, James W., The Organic Chem Lab Survival Manual, 1988, Second Edition, pp. 103–107.*

* cited by examiner

*Primary Examiner*—Thurman K. Page
*Assistant Examiner*—Robert M. Joynes
(74) *Attorney, Agent, or Firm*—Bromberg & Sunstein LLP

(57) ABSTRACT

The present invention relates to a novel solid pharmaceutical formulation containing lovastatin and simvastatin, respectively, with a particle size D(0.9) between 15 and 100 $\mu$m and a specific particle surface area between 1 and 4 m$^2$/g, and to the process for its preparation. The present invention also relates to the method for production of lovastatin and simvastatin with the size of crystals which are suitable for the preparation of the pharmaceutical formulation of the present invention. The novel solid pharmaceutical formulation is useful for treating hypercholesterolemia and hyperlipidemia.

14 Claims, No Drawings

SOLID PHARMACEUTICAL FORMULATION CONTAINING LOVASTATIN AND SIMVASTATIN, RESPECTIVELY, AND ITS PREPARATION

The present application claims priority from Slovenian Patent Application no. P-9900211, entitled "TRDNA FARMACEVTSKA FORMULACUA, KI VSEBUJE LOVASTATIN AND SIMVASTATIN, IN NJENA PRIPRAVA," filed September 10, 1999, which application is incorporated herein by reference.

TECHNICAL FIELD

Lovastatin and simvastatin are known as HMG-CoA reductase inhibitors and are used as antihypercholesterolemic and hypolipidemic agents. Lovastatin is produced by fermentation using microorganisms of different species identified as species belonging to Aspergillus or Monascus, and simvastatin is the product of lovastatin obtained by the methods of chemical synthesis.

The present invention relates to a novel solid pharmaceutical formulation containing lovastatin and simvastatin, respectively, which ensures rapid dissolution of the active substance from the pharmaceutical formulation. The present invention also relates to the process for its preparation.

The present invention also relates to the methods for the production of lovastatin and simvastatin with suitable physical and chemical properties for preparation of the pharmaceutical formulation of the current invention.

Simvastatin and lovastatin are lipophilic molecules of very poor solubility in water. The partition coefficient between octanol and water for lovastatin is about 20 000, for simvastatin about 50 000, which is similar to that of griseofulvin, an antibiotic with well-known dissolution problems. The poor solubility is also suggested by data that at room temperature the volumes of water required to dissolve 20 mg of lovastatin and simvastatin are about 15 liters and 14 liters, respectively, in contrast to equal amounts of fluvastatin and pravastatin, the statin analogs, which dissolve in 10 ml and only 0.07 ml of water, respectively.

The absorption of an active substance in the body following oral administration of a pharmaceutical formulation, particularly from the small and large intestine, is affected primarily by dose size/dissolution rate ratio, dissolution rate, degradation and metabolic conversion in the lumen and effective permeability absorption of an active substance across the intestinal mucosa. The results of the experiments have shown that lovastatin and simvastatin are relatively stable in the intestinal fluid; however, due to their strong lipophilic nature, passage of lovastatin and simvastatin from the small intestine across the intestinal mucosa into the bloodstream is a more serious problem. Lovastatin and simvastatin cross the intestinal mucosa primarily by passive transport (diffusion), and to a smaller extent by active transport (it was suggested from some studies that ATP-dependent transport proteins involved in the transport mechanism in the apical membrane of erythrocytes may recognise lovastatin as a substrate). Apart from the chemical properties of the substance, the rate and extent of passive transport depends primarily on a concentration gradient restored at the intestinal mucosa—higher concentration gradients suggest a more rapid passage of an active substance from the gastrointestinal tract into the body. In spite of the fact that in general, lipophilic substances cross the cellular membranes more easily than hydrophilic substances, it has been shown that the diffusion rate across the membrane in case of more lipophilic substances (partition coefficient octanol/water>1000) was lower than in case of less lipophilic substances (partition coefficient octanol/water<100). One of explanations is an association that at diffusion through the membrane association of the lipophilic substance with membrane lipids occurring at crossing the membrane, which delays passage across membranes.

In case of substances of poor solubility and strong lipophilic character, which cross the membrane only by passive diffusion, dissolution rate of a substance from a particular pharmaceutical formulation is one of the key factors which define the rate and the extent of absorption. The faster a substance dissolves, the higher local concentrations of the substance are, resulting in more rapid passage across the membrane. Relevance of producing high local concentrations of lovastatin and simvastatin has clearly been shown in the tests with extended-release pharmaceutical formulations where the bioavailability of both substances was almost by 50% lower than with immediate-release standard tablets. Lower bioavailability is due to lower local concentrations of the active substance resulting in a smaller flux of the active substance through the intestinal membrane. Measurements of the intestinal membrane absorption following oral lovastatin have shown that only 31% of a total dose crosses the membrane (in case of simvastatin between 60 and 80%) and in spite of a relatively long absorption phase (an active form of lovastatin reaches peak concentration in blood 2.8 hours post-dose), lovastatin has a very low bioavailability primarily due to poor absorption.

Regarding great relevance of sufficiently rapid dissolution of lovastatin and simvastatin from a particular pharmaceutical formulation, for an effective pharmaceutical formulation it is of particular importance that the active substance in the region where drug absorption occurs undergoes rapid dissolution and obtains the highest possible concentration gradient over the shortest possible time. After rapid dissolution of lovastatin and simvastatin, respectively, transport rate of an active substance across the membrane is indirectly greater thereby the effective absorption of an active substance from the alimentary tract is also indirectly increased. The above described facts impose the problem to pharmaceutical technologists how to prepare a pharmaceutical formulation which will facilitate the most efficient absorption of a strongly lipophilic in water poorly miscible active substance.

In our work we have surprisingly found that a size and specific surface area of crystals—particles used for the preparation of a pharmaceutical formulation are the parameters which have an impact on the dissolution rate of lovastatin and simvastatin, respectively from a particular pharmaceutical formulation. Thus, we have found that the bioavailability improved when lovastatin crystals and simvastatin crystals, respectively, with a smaller particle size and a larger specific surface area, are used for the preparation of a particular pharmaceutical formulation. We have noticed that dissolution rate of the active substance from a particular pharmaceutical-formulation was markedly higher if a substance with a smaller particle size and a larger specific surface area was used than when a substance with large size particles and a smaller specific area was used.

The results of our investigations have shown that for the preparation of a pharmaceutical formulation of the present invention, it is advantageous to use lovastatin and simvastatin, respectively, with a particle size D(0.9) between 15 and 100 $\mu$m (D(0.9) denotes a particle size wherein 90% (volume) particles in the substance used are below D(0.9)) and a specific particle surface area between 1 and 4 $m^2/g$ measured by the BET method (S. Brauner: The Adsorption of Gases and Vapours, Princeton, (1945)).

To illustrated the advantage of using lovastatin and simvastatin, respectively, with a smaller particle size and a large specific surface area, we have made two sets of tests. At first we have prepared three samples of lovastatin* with varying particle size and compared dissolution** of those samples in water (Table I).

| Time (min) | A (mg/l) | B (mg/l) | C (mg/l) |
| --- | --- | --- | --- |
| 0 | 0 | 0 | 0 |
| 1 | 0.65 | 0.50 | 0.25 |
| 3 | 0.77 | 0.68 | 0.30 |
| 5 | 0.78 | 0.71 | 0.40 |
| 10 | 0.81 | 0.78 | 0.56 |
| 30 | 0.88 | 0.87 | 0.82 |
| 50 | 0.90 | 0.95 | 0.94 |

*=physical parameters of lovastatin samples

|   | d (0.1) $\mu$m | d (0.5) $\mu$m | d (0.9) $\mu$m | Spec. Pov. $m^2/g$ |
| --- | --- | --- | --- | --- |
| A | 1.6 | 6 | 22 | 3.3 |
| B | 1.4 | 7.9 | 31 | 2.2 |
| C | 17 | 54 | 163 | 0.7 |

**–200 mg of lovastatin sample suspended in 0.1% aqueous solution of Tween 80 (necessary for dispersion of sample) was stirred for 120 min on magnetic stirrer. After that the sample was diluted 100 times and the concentration of lovastatin in the solution was measured at different times.

For the second set of tests we have prepared pharmaceutical formulations of lovastatin with varying particle size and compared dissolution rate of the active substance from it. Table H shows the rates of dissolution of the pharmaceutical formulations containing lovastatin of different particle size and specific surface area in water (the method for preparation of the pharmaceutical formulation is described in Examples 1, 2 and 3).

of the crystals may have a negative impact on the yield of the process and, additionally, it may cause decomposition of unstable substances and therefore new impurities. A better method for the preparation of small size crystals is based on the special apparatus which ensures an extremely high intensity of mixing of fluids and is disclosed in U.S. Pat. No. 5314506. In our work related to the production of lovastatin and simvastatin of the suitable quality for the preparation of a pharmaceutical formulation of the present invention, we have surprisingly found that it is possible to prepare very small size particles (with D(0.9) less than 40 $\mu$m) which provide the best results when lovastatin or simvastatin solutions in water-miscible organic solvents are poured into water. Solvents which provide particles of the smallest size are acetone and methanol. Lovastatin and simvastatin with somewhat larger size particles (D(0.9) greater than 40 and less than 100 $\mu$m) can be obtained using the process wherein water is poured into the lovastatin or simvastatin solution in water-miscible organic solvents.

A solid pharmaceutical formulation of the present invention can be in the form of tablets, film coated tablets, granules or capsules. The ingredients suitable for the preparation of a solid pharmaceutical formulation of present invention include:

a) fillers, such as microcrystalline cellulose, lactose, sugars, starches, modified starch, mannitol, sorbitol and other polyols, dextrin, dextran and maltodextrin, calcium carbonate, calcium phosphate and/or hydrogen phosphate, sulphate;

b) binding agents, such as lactose, starches, modified starch, dextrin, dextran and maltodextrin, microcrystalline cellulose, sugars, polyethylene glycols, hydroxypropyl cellulose, hydroxypropyl methylcellulose, ethylcellulose, hydroxyethylcellulose, methylcellulose, carboxymethylcellulose, croscarmellose sodium, gelatine, acacia gum, tragacanth, polyvinylpyrrolidone, magnesium aluminium silicate;

c) disintegrating agents such as croscarmellose sodium, cross-linked polyvinylpyrrolidone, cross-linked carboxymethyl starch, different starches and microcrystalline cellulose, magnesium aluminium silicate, polyacrylin potassium;

d) glidants such as magnesium stearate, calcium stearate, zinc stearate, calcium behenate, sodium stearyl

TABLE II

| Time (min) | Pharmac. formulation 1 (40 mg) (% of dissolved lovastatin) | Pharmac. Formulation 2 (40 mg) % of dissolved lovastatin) | Pharmac. formulation 3 (40 mg) % of dissolved lovastatin) |
| --- | --- | --- | --- |
| 0 | 0 | 0 | 0 |
| 5 | 46.7 | 49.2 | 33.3 |
| 10 | 71.2 | 71.7 | 57.0 |
| 20 | 90.7 | 89.3 | 81.4 |
| 30 | 96.3 | 95.2 | 91.5 |
| 40 | 98.5 | 98.0 | 96.3 |

Pharmaceutical formulation 1: lovastatin with D(0.9) = 77 $\mu$m and and specific surface area of 1.3 $m^2/g$
Pharmaceutical formulation 2: lovastatin with D(0.9) = 22 $\mu$m and and specific surface area of 3.3 $m^2/g$
Pharmaceutical formulation 3: lovastatin with D(0.9) = 163 $\mu$m and and specific surface area of 0.7 $m^2/g$ Lovastain and simvastatin, which according to their physical parameters are suitable to be used in a pharmaceutical formulation of the present invention, can be prepared by using the conventional methods of crystallisation (giving relatively large crystals—after crystallisation from ethyl acetate crystals with D(0.9) of about 150 $\mu$m are formed) and the crystals obtained are ground to the desired size. Grinding fumarate, talc, magnesium trisilicate, stearic acid, palmitic acid, carnauba wax, silicon dioxide;

e) if required, surface active agents and other conventional components for solid pharmaceutical formulations can be included into the formulation, such as colouring agents, lakes, aromas and adsorbents. As a surface active agent the following may be used: ionic surfactants, such as sodium lauryl sulphate or non-ionic surfactants such as different poloxamers (polyoxyethylene and polyoxypropylene copolymers), natural or synthesised lecithins, esters of sorbitan and fatty acids (such as Span® [Atlas Chemie]), esters of polyoxyethylenesorbitan and fatty acids (such as Tween® [Atlas Chemie]), polyoxyethylated hydrogenated castor oil (such as Cremophor® [BASF]), polyoxyethylene stearates (such as Myrj® [Atlas Chemie]) or any combination of the herein above mentioned surface active agents.

The present invention is illustrated but in no way limited by the following examples.

EXAMPLES

Examples 1–3

The process for the preparation of formulations 1, 2 and 3.

8 kg of lovastatin (with a particle size of D(0.9)=77 and a specific surface area of 1.3 $m^2/g$), 26 kg of lactose, 0.8 kg of croscarmellose sodium, 0.8 kg polyvinylpyrrolidone K25 and 1.38 kg of the triturate (mix 0.08 kg of iron oxide and 1.3 kg of lactose and pass through the mill) were blended in a high-speed blender. The dry mixture was granulated with 3.82 kg of granulating solution (dissolve 0.02 kg of BHA in 1.4 kg of ethanol while mixing in the high-speed blender and add 2.4 kg of demineralized water to the resulting solution). The granulation was dried in a bed-fluid dryer at the inlet air temperature to 45° C. Drying was carried out (between 20 and 40 minutes) until the moisture of the granulation below 1%, measured 20 minutes at 100° C., was obtained. The dried granulation was sieved in a 0.8 mm sieve to obtain granulation particles of the desired size. To the dried, sieved granulation 2 kg of mannitol, 0.8 kg of croscarmellose sodium, 0.2 kg of calcium stearate were added, the mixture was homogenised and pressed to tablets on a rotary tablet press. Tablets individually had a diameter of 8.0 mm and weighed 200 mg.

For the preparation of formulation 2, lovastatin with a particle size of D(0.9)=22 and a specific surface area of 3.3 $m^2/g$ was used; for formulation 3, lovastatin with a particle size of D(0.9)=163 and a specific particle surface area of 0.7 $m^2/g$ was used.

Example 4

Lovastatin (18.08 kg) was dissolved in 1080 liters of ethyl acetate and concentrated to the volume of 180 liters on a rotary evaporator at 35° C. The resulting concentrate was cooled to 10° C. and crystals were formed. The crystals formed were filtered and dried. A measured size of the formed lovastatin crystals was D(0.9)=163 µm, and a specific surface area 0.7 $m^2/g$.

Example 5

4.6 g of lovastatin were dissolved in 50 ml of dimethylformamide and 100 ml of water was poured into the resulting solution. The crystals formed were filtered and dried. A measured size of the formed lovastatin crystals was d(0.9)= 77 µm, and a specific surface area 1.3 $m^2/g$.

Example 6

2 kg of lovastatin were dissolved in 120 liters of methanol and the resulting solution was poured into 180 liters of water. The crystals formed were filtered and dried. A measured size of the formed lovastatin crystals was D(0.9)=22 µm, and a specific surface area 3.3 $m^2/g$.

Example 7

An example for the preparation of capsule.

0.5 g of butylhydroxyanisole was dissolved in 10 g of ethanol while mixing in a high-speed blender. 200 mg of lovastatin with a particle size of D(0.9)=22 and a specific particle surface area of 3.3 $m^2/g$ and 796 g of lactose were mixed in a suitable mixer and the resulting dry mixture was poured with the prepared solution of butylhydroxyanisole in ethanol. To the mixture 4 g of calcium stearate were added and the mixture obtained was sieved in a 0.8 mm sieve. The resulting mixture was filled into hard gelatine capsules size 3, each capsule containing 40 mg of lovastatin. Capsules containing different amounts of the active substance, for example between 5 and 80 mg per capsule, can be prepared by varying the capsule size and the amount of the mixture used for capsule filling.

What is claimed is:

1. A process for preparation of simvastatin or lovastatin in the form of crystals with D(0.9)<40 µm, wherein a solution of lovastatin or simvastatin in a water miscible organic solvent is poured into water.

2. A process for the preparation of simvastatin or lovastatin in the form of crystals with D(0.9)<40 µm according to claim 1, wherein the organic solvent is ethanol, methanol, acetonitrile, acetone, or dimethylformamide.

3. A process for the preparation of simvastatin or lovastatin in the form of crystals with D(0.9)>40 and <100 µm, wherein water is poured into a solution of lovastatin or simvastatin in a water miscible organic solvent.

4. A process for the preparation of simvastatin or lovastatin according claim 3, wherein the organic solvent is ethanol, methanol, acetonitrile, acetone or dimethylformamide.

5. A process for preparation of a solid pharmaceutical formulation for the treatment of hypercholesterolemia, which comprises:
   (a) preparing crystals of the active substance lovastatin or simvastatin having D(0.9) between 15 and 100 µm with a specific surface area between 1 and 4 $m^2/g$ by
      (i) pouring a solution of lovastatin or simvastatin in a water miscible organic solvent into water or by pouring water into the solution of lovastatin or simvastatin in the water miscible organic solvent,
      (ii) filtering the crystals formed, and
      (iii) driying the crystals;
   (b) preparing a dry mixture, which comprises:
      (i) the active substance lovastatin or simvastatin in the form of crystals with D(0.9) between 15 and 100 µm and with a specific surface area between 1 and 4 $m^2/g$;
      (ii) one or more compounds selected from the group consisting of fillers, binding agents, disintegrating agents, and glidants; and
   (c) processing the dry mixture into the form of a tablet, film-coated tablet, granule, or capsule.

6. A process for the preparation of a solid pharmaceutical formulation for the treatment of hypercholesterolemia according to claim 5, wherein the organic solvent of (a) is ethanol, methanol, acetonitrile, acetone, or dimethylformamide.

7. A process for preparation of a solid pharmaceutical formulation for the treatment of hypercholesterolemia, which comprises:
   (a) preparing crystals of the active substance lovastatin or simvastatin having D(0.9)<40 µm by
      (i) pouring a solution of lovastatin or simvastatin in a water miscible organic solvent into water.
      (ii) filtering the crystals formed, and
      (iii) driying the crystals;

(b) preparing a dry mixture, which comprises:
  (i) the active substance lovastatin or simvastatin in the form of crystals with D(0.9)<40 μm;
  (ii) one or more compounds selected from the group consisting of fillers, binding agents, disintegrating agents, and glidants; and
(c) processing the dry mixture into the form of a tablet, film-coated tablet, granule, or capsule.

8. A process for preparation of a solid pharmaceutical formulation for the treatment of hypercholesterolemia, which comprises:
  (a) preparing crystals of the active substance lovastatin or simvastatin having D(0.9) in the range from 40 μm to 100 μm by
    (i) pouring water into a solution of lovastatin or simvastatin in a water miscible organic solvent,
    (ii) filtering the crystals formed, and
    (iii) drying the crystals;
  (b) preparing a dry mixture, which comprises:
    (i) the active substance lovastatin or simvastatin in the form of crystals with D(0.9) in the range from 40 μm to 100 μm;
    (ii) one or more compounds selected from the group consisting of fillers, binding agents, disintegrating agents, and glidants; and
  (c) processing the dry mixture into the form of a tablet, film-coated tablet, granule, or capsule.

9. A process according to claim 5, wherein the dry mixture of (b) further comprises:
  (iii) one or more compounds selected from the group consisting of surface active agents and combinations thereof, coloring agents, lakes, aromas, and adsorbents.

10. A process for the preparation of a solid pharmaceutical formulation for the treatment of hypercholesterolemia according to claim 7, wherein the organic solvent of (a) is ethanol, methanol, acetonitrile, acetone or dimethylformamide.

11. A process according to claim 7, wherein the dry mixture of (b) further comprises:
  (iii) one or more compounds selected from the group consisting of surface active agents and combinations thereof, coloring agents, lakes, aromas and adsorbents.

12. A process for the preparation of a solid pharmaceutical formulation for the treatment of hypercholesterolemia according to claim 8, wherein the organic solvent of (a) is ethanol, methanol, acetonitrile, acetone or dimethylformamide.

13. A process according to claim 8, wherein the dry mixture of (b) further comprises:
  (iii) one or more compounds selected from the group consisting of surface active agents and combinations thereof, coloring agents, lakes, aromas and adsorbents.

14. A process for preparation of a solid pharmaceutical formulation for the treatment of hypercholesterolemia, which comprises:
  (a) preparing crystals of the active substance lovastatin or simvastatin having D(0.9) in the range from 40 μm to 100 μm by
    (i) pouring water into a solution of lovastatin or simvastatin in a water miscible organic solvent,
    (ii) filtering the crystals formed, and
    (iii) drying the crystals;
  (b) preparing a dry mixture, which comprises:
    (i) the active substance lovastatin or simvastatin in the form of crystals with D(0.9) in the range from 40 μm to 100 μm;
    (ii) one or more compounds selected from the group consisting of fillers, binding agents, disintegrating agents and glidants;
    (iii) one or more compounds selected from the group consisting of surface active agents and combinations thereof, coloring agents, lakes, aromas and adsorbents; and
  (c) processing the dry mixture into the form of a tablet, film-coated tablet, granule or capsule.

* * * * *

UNITED STATES PATENT AND TRADEMARK OFFICE
CERTIFICATE OF CORRECTION

PATENT NO. : 6,696,086 B1
DATED : February 24, 2004
INVENTOR(S) : Zlatko Pflaum et al.

It is certified that error appears in the above-identified patent and that said Letters Patent is hereby corrected as shown below:

Column 6,
Line 44, replace "driying" with -- drying --.
Line 66, replace "water." with -- water, --.
Line 68, replace "driying" with -- drying --.

Signed and Sealed this

Twenty-fifth Day of May, 2004

JON W. DUDAS
*Acting Director of the United States Patent and Trademark Office*